(12) United States Patent
Vieth et al.

(10) Patent No.: US 9,066,958 B2
(45) Date of Patent: Jun. 30, 2015

(54) VITAMIN D COMPOSITIONS AND METHOD OF ADMINISTRATION TO A HUMAN BEING

(76) Inventors: Reinhold W. Vieth, Toronto (CA); Elaine Vieth, Toronto (CA)

( * ) Notice: Subject to any disclaimer, the term of this patent is extended or adjusted under 35 U.S.C. 154(b) by 1815 days.

(21) Appl. No.: 11/674,234

(22) Filed: Feb. 13, 2007

(65) Prior Publication Data

US 2008/0069925 A1    Mar. 20, 2008

(30) Foreign Application Priority Data

Sep. 14, 2006  (CA) .................................... 2558202

(51) Int. Cl.
*A61K 31/59*    (2006.01)
(52) U.S. Cl.
CPC .................................... *A61K 31/59* (2013.01)
(58) Field of Classification Search
None
See application file for complete search history.

(56) References Cited

U.S. PATENT DOCUMENTS

| | | | |
|---|---|---|---|
| 3,149,037 A * | 9/1964 | Bauernfeind et al. | 514/167 |
| 4,248,867 A | 2/1981 | Ikushima | |
| 5,532,229 A | 7/1996 | Vieth | |
| 5,601,605 A * | 2/1997 | Crowe et al. | 606/236 |
| 5,620,462 A | 4/1997 | Valenti | |
| 6,638,978 B1 * | 10/2003 | Kabara | 514/550 |
| 2003/0099747 A1 | 5/2003 | Eini | |
| 2003/0104078 A1 | 6/2003 | Barrett-Reis | |
| 2003/0191093 A1 | 10/2003 | Chen | |

FOREIGN PATENT DOCUMENTS

| | | | |
|---|---|---|---|
| CA | 2111271 A1 | 6/1994 | |
| CA | 2315224 A1 | 6/1999 | |
| CA | 2393357 A1 | 2/2003 | |
| CA | 2122431 | 10/2006 | |
| CA | 2558202 A1 | 11/2006 | |
| CA | 2578881 A1 | 7/2007 | |
| WO | 0054838 A1 | 9/2000 | |

OTHER PUBLICATIONS

Fliszar et al. (J Pharma Biomed Anal, 40: 896-900, 2006).*
Vieth (http://www.direct-ms.org/pdf/VitDVieth/Vieth%20Anthropology%20vit%20D.pdf, Jan. 2006).*
Blass et al., Pain, 83: 611-623, 1999.*
Schleithoff et al., "Vitamin D supplementation improves cytokine profiles ion patients with congestive heart failure: a double-blind, randomized placebo-controlled trial", *Am J Clin Nutr*, 2006, pp. 754-759, vol. 8.
Holmberg et al., "Absorption of a Pharmacological Dose of Vitamin $D_3$ From Two Different Lipid Vehicles in Man: Comparison of Peanut Oil and a Medium Chain Triglyceride", *Biopharmaceutics & Drug Disposition*, 1990, pp. 807-815, vol. 11.
Supplementary European Search Report for corresponding European application (completed Jan. 12, 2012).
Greer et al., Effects of Increased Calcium, Phosphorus, and Vitamin D Intake on Bone Mineralization in Very Low-Birth-Weight Infants Fed Formulas with Polycose and Medium-Chain Triglycerides, The Journal of Pediatrics, vol. 100, No. 6, Dec. 31, 1982, pp. 951-955.
Scanlon, Vitamin D Expert Panel Meeting—Final Report, CDC Expert Panel Meeting, Oct. 11, 2001, retrieved from the Internet at URL http://www.cdc.gov/nccdphp/dnpa/nutrition/pdf/Vitamin_D_Expert_Panel_Meeting.pdf, p. 21 (retrieved on Dec. 13, 2011).
European Phamracopoeia 4.0, Dec. 31, 2001, Directorate for the Quality of Medicines of the Council of Europe, pp. 2071-2072.
Hart et al., Final Report of the Color Additive Scientific Review Panel, Risk Analysis, vol. 6, No. 2, 1986, p. 117-154.
Wikipedia "Hypervitaminosis D", URL http://en.wikipedia.org/wiki/Hypervitaminosis_D, p. 1-8, (2010).

* cited by examiner

*Primary Examiner* — Bong-Sook Baek
(74) *Attorney, Agent, or Firm* — Jeffrey S. Melcher; Manelli Selter PLLC

(57) ABSTRACT

Composition of vitamin D in medium-chain triglycerides and use thereof in delivering a nutritional or therapeutic amount of vitamin D to a human being, particularly, an infant. The compositions are applied to an object, such as skin or in the case of an infant to a woman's nipple or pacifier from which the infant sucks off the composition. The method provides a more suitable, safer and efficient way of providing the human being with vitamin D. The compositions further comprise a free fatty acid and/or monoglyceride, oxidant preservative and, optionally, other vitamins.

12 Claims, No Drawings

US 9,066,958 B2

VITAMIN D COMPOSITIONS AND METHOD OF ADMINISTRATION TO A HUMAN BEING

This application claims foreign priority under 35 U.S.C. 119 to Canadian Patent Application Serial No. 2,558,202, filed 14 Sep. 2006.

FIELD OF THE INVENTION

This invention relates to compositions comprising vitamin D in a medium-chain triglyceride medium and use thereof for human beings, particularly, breast-feeding infants.

BACKGROUND TO THE INVENTION

A balanced level of vitamin D has long been recognized as essential to health. Vitamin D appears to increase the efficiency of the intestines to absorb calcium and also mobilizes calcium from bone tissue when required. A deficiency in vitamin D leads to rickets, a debilitating bone disease while excessive intakes of vitamin D are toxic.

The skin is the major site of cholesterol production and humans acquire vitamin D through the natural action of ultraviolet light on the skin. 7-Dehydrocholesterol, which is unstable to ultraviolet light, is normally a precursor to cholesterol. However, ultraviolet light breaks open the B-ring of the 7-dehydrocholesterol molecule to generate previtamin D3, which spontaneously isomerizes over hours and days into vitamin D3, which is also known as cholecalciferol. An unknown proportion of the vitamin D from the skin is absorbed into the circulation. Vitamin D3 is not soluble in water, and in the circulation, there is a protein that specifically binds to and carries vitamin D and its metabolites. The advantage of ultraviolet exposure is that it is natural, and has no vitamin D toxicity associated with it. The disadvantage is that the availability of ultraviolet light is unreliable, and too much of it causes sunburn or skin cancer. At northern latitudes there is often not enough ultraviolet light intensity outdoors to generate previtamin D.

For biological activity, vitamin D must go through two metabolic steps. Vitamin D is metabolized by the liver to 25-hydroxyvitamin D [25(OH)D], which is measured in serum to reflect vitamin D nutritional status. 25-hydroxyvitamin D per se has little biological activity. The kidney metabolizes 25-hydroxyvitamin D into the active hormone, 1, 25-dihydroxyvitamin D, which affects calcium transport across cell membranes. The body, according to its mineral requirements, carefully regulates production and breakdown of 1,25-dihydroxyvitamin D to regulate plasma calcium concentrations. Very few foods naturally contain vitamin D. Mellanby, J Physiol (London) volume 52:1iii (1919), instituted the idea that an artificial supplement, cod-liver oil, contained an agent that prevented rickets; the agent became known as vitamin D. Most of the vitamin D in our food is supplementary, synthetic material, which is either in the form of vitamin D3, the form naturally produced in animals, or it can be vitamin D2, which is derived from a plant steroid. The term, vitamin D, refers to either the vitamin D2 or vitamin D3 forms.

Pediatric associations in Canada and the United States now strongly encourage starting vitamin D supplementation from birth onwards (Health Canada, Vitamin D supplementation for breastfed infants). Breast-feeding results in fewer infections and allergies during the first year of life compared to babies fed formula. Breast milk provides nearly optimal nutrition for newborns; however, it provides little vitamin D. Vitamin D has well-recognized effects on bone, but beyond that, better vitamin D nutrition during infancy is associated with less risk of other diseases that develop later in life. These disease reductions include less risk of juvenile diabetes, and schizophrenia (Hypponen, E., Laara, E., Reunanen, A., Jarvelin, M. R., and Virtanen, S. M. (2001) Lancet 358, 1500-1503) (McGrath, J., Saari, K., Hakko, H., Jokelainen, J., Jones, P., Jarvelin, M. R., Chant, D., and Isohanni, M. (2004) Schizophr. Res. 67, 237-245). However, because it is normally obtained through sun exposure instead of orally, vitamin D is the one nutrient that is most often deficient in breast milk (Centers for Disease Control, Vitamin D Expert Panel Meeting, Oct. 11-12, 2001 Atlanta, Ga. Final Report).

In 2005, the American Academy of Pediatrics issued a new policy statement concerning breast-feeding (American Academy Of Pediatrics Policy Statement 2005; Pediatrics 115; 496-506). One major change was that all breast-fed infants should receive 200 IU (5 mcg) of oral vitamin D drops daily, beginning during the first 2 months of life. The older recommendation had been that vitamin D supplementation should start at around 2 months of life. The latest American Academy of Pediatrics recommendation follows what Health Canada has been advising, that vitamin D supplementation should be from birth, with 400 IU (10 mcg) of vitamin D per day (Pediatrics 2005; 115; 496-506). Moreover, Health Canada recommends that infants in the north be given 800 IU (20 mcg) of vitamin D per day.

The need to provide vitamin D at an earlier age makes the problem of providing vitamin D nutrition more complicated. Smaller infants are more difficult to handle. Furthermore, breast-feeding mothers may not want to give their infants foreign liquids or compounds that are not natural for them to be taking. What makes the problem worse, is that the recommendations from pediatric societies and government bodies provide no detail or any method for exactly how to give vitamin D to the breast-feeding infant. They simply advise that parents should be giving vitamin D.

Existing products, approved in Canada and the United States for the purpose of infant vitamin D nutrition require the use of one-half to one mL of a detergent-solublized aqueous liquid emulsion. The liquid is either given directly into the mouth, or mixed into milk or to other food consumed by the infant. Instructions for administering vitamin D drops typically involve inserting the dropper containing the liquid product directly into the baby's mouth.

Parents of infants express great frustration about existing products and methods for providing infants with vitamin D, especially about the taste and the fact that infants often spit out at least some of the liquid. Direct administration of liquid vitamin D preparations is commonly done with an eyedropper, and with the infant lying on its back. One risk associated with direct administration of vitamin D solutions into the mouth is that infants can gag on, or inhale some of the liquid.

Vitamin D liquid drops usually contain other vitamins as well. One milliliter of these products contains 400 IU (10 mcg) of vitamin D. The aqueous vitamin D drops have only a 50-day shelf-life once the bottle is opened. They contain ingredients foreign to infant nutrition, and there are many complaints about the taste. One major problem is that infants spit out the 1 mL liquid vitamin drops. This creates a mess and the dose delivered to the infant is unreliable. For any therapeutic protocol, inconvenience, risk, and difficulty with administration result in lower compliance rates. Poor compliance results in under-dosing, and ineffective treatment. These factors also diminish nutrient supplementation with vitamin D. There are vitamin D drops available in oil, at 400 IU per drop in the United States (naturalhealthsupply.com). The vitamin D for this is dissolved in olive oil and/or corn oil and/or sesame or flax-seed oil. The problem with these is that the oils are comprised of long-chain unsaturated fatty-acid triglycerides that will become rancid with repeated opening of the container, they carry a flavor, and they have a greasy feel on a pacifier. Moreover, no product like this is advised for, nor advocated, nor used in any way for nutrition of the breast-feeding infant.

One prescription product contains vitamin D in an unspecified oil, (20,000 IU (500 mcg) per mL of oil). The method for use involves mixing two drops into to two drops in milk or mash. This is not a practical way to provide vitamin D for breast-fed infants younger than two months of age, because it presumes that nutrition is provided by some means other than the breast. Furthermore, this method is no different from what is done in North America with the 1-mL per day liquid vitamin drops that are administered to infants by mixing into milk or food by the same method.

U.S. Pat. No. 5,532,229, issued Jul. 2, 1996 to Vieth, Reinhold W., and Canadian Patent No. 2,122,431, issued Oct. 10, 2006 to Vieth, Reinhold W., describe a method of delivering vitamin D to the blood of a mammal by topically administering to the skin of the mammal, vitamin D in a solution. In principle, this method could be used to provide vitamin D to infants, via the skin, which is a safe and natural route of entry for this nutrient. For example, a skin lotion that contains vitamin D can be absorbed over time through the skin of the infant. For example, medium-chain triglycerides are useful as a skin lotion, and at the same time they can function as a solvent to deliver vitamin D. However, the efficacy of vitamin D delivery is problematic with this approach, because vitamin D could be wiped easily off the skin before it could be absorbed into the body.

U.S. Pat. No. 4,248,867, issued to Ikushima et al on Feb. 3, 1981 describes a method for manufacturing an oily preparation which comprises irradiating a triglyceride of saturated middle chain fatty acid(s) with light longer than 290 nm. This process alters the oil to be a solvent in which a selection of 1-alpha-hydroxy-vitamin Ds in the treated triglyceride can be dissolved and remain stable. These 1-hydroxy vitamin D's are either diol or triol compounds which are fundamentally different from vitamin $D_2$ and vitamin $D_3$.

Notwithstanding the above teachings of the prior art, there remains a need for a safe, convenient and efficacious method of administering nutritional or therapeutic amounts of vitamin D to a human being, particularly, a suckling infant. There is also a utility for adults to be able to deliver a dose of vitamin D efficiently by sucking a vitamin supplement from a surface, instead of directly placing the supplement directly into the mouth.

SUMMARY OF THE INVENTION

In this specification and claims, the compound "vitamin D" means (5Z-7E)-(3S)-9,10-seco-5,7,10(19)-cholestatrien-3-ol also having the trivial names cholecalciferol or calciol (D3); and ergocalciferol (D2).

It is an object of the present invention to provide an improved, suitable, safer and efficient method of providing a nutritional or therapeutic effect amount of Vitamin D to a human being, particularly, a suckling infant.

It is a further object is to provide Vitamin D compositions for use in said method.

A composition and method has been developed which involves the application of a vitamin D composition to a human being from the surface of an object that is a suitable and efficient method of administration of a desired amount of vitamin D to the human being.

The human being may be an adult or an infant. The term "infant" in this specification includes babies and small children, and the term "adult" includes non-small children.

In the case of administration of the compositions according to the invention to an infant, the method comprises the application of, preferably, one drop of a solution of vitamin D in a suitable, biologically-acceptable oil carrier in the case of an infant onto a mother's nipple or onto a pacifier, and placing it into the mouth of an infant for, preferably, at least 30 seconds, to suck the vitamin D composition off the nipple or pacifier, to thereby consume the vitamin D. In the case of an adult, one or more drops may be applied to the skin of an arm or a knuckle of the hand of the adult who then licks or sucks the composition from the skin.

We have found that the difficulties with the aforesaid previous ways of providing vitamin D to an infant can be overcome by the process of application of vitamin D in a one-drop (about 33 microliter) volume of medium-chain triglyceride oil onto a pacifier or nipple and into the mouth of a suckling infant. This process of nipple or pacifier application eliminates the need to risk over-exposure of the infant to ultraviolet light in order to acquire in vivo vitamin D. Furthermore, the process of nipple or pacifier application eliminates the need to administer vitamin D directly into the mouth with a dropper, or in a larger volume that infants commonly spit out or gag on, or have to take with food.

The process of the present invention can improve compliance by parents to government and medical recommendations to supplement their infants with vitamin D. Implementation of the invention to improve vitamin D supplementation may lower risk of disease for the infant, which, on a broader scale, should benefit public health.

It is highly desirable, though not an essential consideration, that the medium-chain triglyceride is a natural constituent of breast milk since such oil use does not introduce a compound foreign to breastfeeding. Furthermore, medium-chain triglycerides are naturally present in milk fat and are hydrolyzed by lipase present in the saliva of the infant. The medium-chain free fatty acids and monoglycerides released by the action of lipase in the saliva of the infant provide the additional benefit of an antimicrobial action, and play a role in resistance to infectious diseases (M. K. M. Nair 2005 J. Dairy Sci. 88:3488-3495)(CQ Sun 2002 Chemico-Biological Interactions 140: 185-198)(AC Pedersen, A Bardow, SB Jensen, B Nauntofte 2002. Oral Diseases 8:117-129).

Thus, in a preferred aspect, the compositions of the present invention may further comprise said free fatty acids, particularly $C_6$-$C_{12}$ carbon-chain compounds, to provide an antimicrobial effect.

We have found that the inventive method of indirect application of vitamin D to a pacifier or nipple, or knuckle can provide vitamin D nutrition to a human with an efficiency of vitamin D delivery by sucking that is in the range acceptable for accuracy of a supplement product labeled dose, with about 4% loss as residual vitamin D remaining on the nipple or pacifier, compared to direct placement of vitamin D into the mouth.

The vitamin D compositions of use in the invention may further comprise an antioxidant to serve as a preservative for the vitamin D, or to provide additional nutrition. Examples of such fat-soluble nutrients are vitamin E, vitamin A, vitamin K, or carotene.

The amount of vitamin D in the composition of use in the practice of the invention may be readily selected to be that amount which provides suitable effects on the circulating concentration of 25-hydroxyvitamin D. For example, a daily single dose on a nipple or pacifier may contain from 2-300 mcg per drop (equivalent to 60 mcg/mL to 9,000 mcg/mL of oil), preferably 5 to 20 mcg per drop (150 mcg/mL to 600 mcg per mL). The stronger compositions are useful for pediatricians who could use them to provide vitamin D as a single-drop dose at each monthly neonatal visit. Thereby, the mother, herself, would not have to deal with vitamin D application.

Accordingly, in one aspect the invention provides a composition comprising vitamin D in liquid, triglycerides of 6 to 12 carbon chain lengths medium for use in delivering a nutritional or therapeutic amount of said vitamin D to a human being from the surface of an object having said composition on said surface to be sucked from said surface by said human being.

Preferably, the composition comprises 9 to 9,000 mcg/ml vitamin D and, more preferably, 150 to 450 mcg/ml vitamin D.

The medium chain triglycerides of use in the practice of the invention have carbon-chain lengths of 6-12 and, preferably, the composition medium comprises at least 95% triglycerides having a carbon-chain length selected from 8-10.

Medium-chain triglycerides are obtained from the oil extracted from the hard, dried fraction of the endosperm of *Cocos nucifera* L. or from the dried endosperm of *Elaeis guineensis* Jacq. They consist of a mixture of triglycerides of saturated fatty acids, mainly of caprylic acid ($C_8H_{16}O_2$) and of capric acid ($C_{10}H_{20}O_2$). They contain not less than 95 percent of saturated fatty acids having 8 to 10 carbon atoms. The substance is a clear solution.

In a most important embodiment, the invention provides a composition as hereinabove defined for use in delivering a nutritional or therapeutic amount of said vitamin D directly into the mouth of an infant from the surface of an object having said composition on said surface to be sucked from said surface by said infant.

Fatty acid composition—The fatty acid fraction of medium-chain triglycerides exhibits the following composition, as determined in the section *Fatty Acid Composition*. Any peak with an area less than 0.05% of the total area, was disregarded.

| Carbon-Chain Length | Number of Double Bonds | Percentage (%) |
|---|---|---|
| 6 | 0 | ≤2.0 |
| 8 | 0 | 50.0-8.0 |
| 10 | 0 | 20.0-50.0 |
| 12 | 0 | ≤3.0 |
| 14 | 0 | ≤1.0 |

To be useful in the practice of the present invention, the vitamin D containing medium, needs to meet many of the aforesaid criteria. Surprisingly we have discovered that the medium-chain triglycerides satisfy these criteria.

In preferred embodiments, the invention provides a composition as hereinabove defined further comprising a compound selected from the group consisting of a free fatty acid and a monoglyceride, preferably, a composition wherein the compound is selected from the group consisting of caprylic acid, caprylic monoglyceride and monocaprylin, at a concentration selected from 0.1 to 20 w/w % medium, preferably, 1 to 10% w/w % medium.

In further preferred embodiments, the invention provides an oxidant preservative, and/or a nutritionally effective amount of a fat-soluble vitamin selected from the group consisting of alpha-tocophenol (vitamin E), vitamin A, vitamin K and B-carotene.

In a further aspect, the invention provides use of a composition as hereinabove defined for the use in delivering a nutritional or therapeutic amount of vitamin D directly from the surface of an object having the composition thereon to be licked or sucked therefrom by a human being, particularly, an infant.

In a particular aspect, the invention provides a method of using a composition as hereinabove defined comprising (i) applying said composition to a surface of an object; and (ii) inserting said object into the mouth of an infant as to allow said infant to suck said composition from said object surface.

Most preferably, in the case of an infant, the object is a woman's nipple or a pacifier

DETAILED DESCRIPTION OF PREFERRED EMBODIMENTS

In order that the invention may be better understood, preferred embodiments will now be described by way of example only.

EXAMPLE 1

The medium-chain triglycerides of use in this invention are liquids that are sufficiently viscous so that one drop does not immediately drip or roll away from the part of the nipple or pacifier that enters the mouth of an infant. The liquid does not coat or adhere to the pacifier so as to prevent efficient removal of the vitamin D from the nipple or pacifier through sucking. The liquid has minimal sensory effects i.e. it has minimal smell, taste, or texture i.e. no oily feel. The liquid is biologically natural in the context of breast-feeding, and is safe for infant consumption. The liquid per se is not subject to rancidity or oxidation over the shelf-life of the composition. Further, it is a medium in which vitamin D does not degrade and, thus, allows of a long shelf life for vitamin D.

This experiment involved the study of a number of liquids to determine their efficiency in the practice of the invention.

One drop of each liquid was applied onto a nipple to determine whether it would adhere well enough so that no portion of it would drip off in a timeframe of 10 seconds. The results of these experimental observations are presented in Table 1 along with further considerations regarding the parameters desired for this invention.

TABLE 1

Experimental observation of potential liquids for suitability for nipple vitamin D

| Vehicle for vitamin D | Experiment drop behavior on nipple# | Taste# | mouth-feel# | taste# | Stability of vitamin D in vehicle | Stability of solvent with storage# | present in breast milk |
|---|---|---|---|---|---|---|---|
| Water | drips off | None | none | none | Poor# | Stable | Yes |
| water-based emulsion (D-vi-sol) | drips off | Yes | no feel | strong taste | 50-days on opening* | Stable | No |

TABLE 1-continued

Experimental observation of potential liquids for suitability for nipple vitamin D

| Vehicle for vitamin D | Experiment drop behavior on nipple[#] | Taste[#] | mouth-feel[#] | taste[#] | Stability of vitamin D in vehicle | Stability of solvent with storage[#] | present in breast milk |
|---|---|---|---|---|---|---|---|
| Ethanol | drips off | Yes | no feel | strong taste | Solvent concentration[#] | Evaporates | No |
| Canola oil | Adheres | Mild | Oily | mild | Stable | Oxidizes/rancidity | No |
| Olive oil | Adheres | Yes | Oily | mild | Stable | Oxidizes/rancidity | No |
| Sesame oil | Adheres | Yes | Oily | strong taste | Stable | Oxidizes/rancidity | no |
| Eitamin E acetate oil | Adheres | None | Oily | none | Uncertain | Stable | no |
| Medium-chain triglyceride | Adheres | None | slightly oily | none | stable >3 yr[#] | Stable | yes |

[#]Direct experimental observation.
*Mead-Johnson published stability statement for D-vi-sol.

Water based preparations and alcohol did not adhere to the nipple. The oil vehicles all adhered to the nipple well enough to make them suitable for handling during breastfeeding or for use of a pacifier. However, residual oily feel on the pacifier was interpreted as a sign of incomplete uptake of the drop with its dose from the pacifier. We found that medium-chain triglyceride oil was particularly desirable.

EXAMPLE 2

This experiment was to determine the efficacy of the uptake of vitamin D in the composition and method through the mouth by sucking and into the body.

A further problem that needed to be addressed was the matter of whether vitamin D dissolved in a liquid vehicle would be removed by sucking and enter the body of the human in an efficacious manner. For this, vitamin D in a solution of medium-chain triglyceride was applied, according to the invention, to pacifiers. One drop of an approximate volume of 33 microliters was applied onto pacifiers, Gerber Nuk™ sizes 1 (small, for newborns) and 3 (for older infants). As the measure of 100% recovery, 33 microliters of vitamin D in medium-chain triglyceride (60,000 IU/33 microliters) was added to 50 mL ethanol directly, or placed onto a pacifier, which was placed in ethanol. To estimate efficiency of removal of the vitamin D, pacifiers were sucked by humans for 30 seconds, and the pacifier was then placed entirely into an 80-mL beaker containing 50 mL ethanol to extract remaining vitamin D. It is important to note that the extraction of remaining vitamin D from the pacifier into ethanol was not immediate. The pacifiers were extracted for 30 min, otherwise measurement of the remaining vitamin D would have been underestimated, with overestimation of efficiency of delivery into the mouth. High-pressure liquid chromatography with absorbance detection at 265 nm of 100 microliters of the ethanol extracts from each of seven such experiments showed that vitamin D remaining on the pacifier comprised a mean of 4%+/−2% SD of the vitamin D applied to the pacifier. Therefore, delivery of the vitamin D applied to a pacifier or to a nipple and taken up into the mouth within half a minute is sufficiently reproducible and complete so as to permit a dose printed on the label of a vitamin supplement product to be claimed as being accurate. Government regulations mandate that vitamin supplements for humans must provide between 90% and 120% of the labeled doses. The dosage loss with the method according to the invention, is accommodated inside that acceptable range, so that the dose that the label states to be present in one drop of product is an appropriate measure of the dose delivered into a human.

EXAMPLE 3

This experiment shows that if the invention truly functioned as intended, the serum 25-hydroxyvitamin D [25(OH)D] should increase in response to the intake of vitamin D according to this invention.

Vitamin $D_3$ was added to medium-chain triglyceride oil to a concentration of 0.4 g per 10 mL. One drop of this had a volume of 33 microliter, and contained 1500 mcg of vitamin $D_3$. This is a relatively high dose which was used to elicit a rapid 25(OH)D response that could not be attributed to other factors. Three humans, who had not taken vitamin D supplements during the previous month each sucked on a pacifier for 30 sec, Gerber Nuk™-brand pacifiers, to which one drop of the vitamin $D_3$ solution in medium-chain triglyceride oil had been applied. Blood samples had been drawn prior to the experiment, and 48 h after taking the dose of vitamin D according to the present invention. Without vitamin D, there could have been no detectable change in serum 25(OH)D concentration in the short timeframe of 48 h. We found that the serum 25(OH)D increased in each human. In the three humans, the mean increase from baseline was 12 nmol/L (the individual increases in serum 25(OH)D were 5, 10 and 20 nmol/L). The results were consistent with the uptake of the vitamin D from the pacifier into the human body. This experiment confirmed the efficacy of the method of the present invention.

EXAMPLE 4

Crystalline vitamin $D_3$ (cholecalciferol, United States Pharmacopea grade) was dissolved into oil of medium chain triglyceride (United States Pharmacopea grade), to make a solution, according to the invention, containing 300 mcg vitamin D per one mL of oil. This composition was bottled in a glass container closed with a Eurodropper cap, with an opening designed to dispense 30 drops per one mL of oil. A breast-feeding mother applied one drop of the solution to the nipple just before offering her breast to her infant to suckle. To ensure complete delivery of the dose, the infant sucked for 30 seconds.

EXAMPLE 5

Crystalline vitamin D3 (cholecalciferol, United States Pharmacopea grade) was dissolved into oil of medium chain triglyceride (United States Pharmacopea grade), to make a solution, according to the invention, containing 300 mcg vitamin D per one mL of oil. This composition was bottled in a plastic container with a dropper opening to dispense one drop of oil. A mother applied one drop of the solution to a pacifier or the nipple of a baby bottle just before putting it into the mouth of her infant to suck. To ensure complete delivery of the dose, the infant sucked for 30 seconds.

EXAMPLE 6

Crystalline vitamin D3 (cholecalciferol, United States Pharmacopea grade) was dissolved into an oil of medium chain triglycerides (United States Pharmacopea grade), to make a solution containing 300 mcg vitamin D per one mL of oil. This was bottled in a glass container closed with a Euro-dropper cap, with an opening designed to dispense 30 drops per one mL of oil. The human being applied one drop of the solution to a knuckle of a hand from which the vitamin D was sucked into the mouth. To ensure complete delivery of the dose, the human sucked for 30 seconds.

Although this disclosure has described and illustrated certain preferred embodiments of the invention, it is to be understood that the invention is not restricted to those particular embodiments. Rather, the invention includes all embodiments which are functional or mechanical equivalents of the specific embodiments and features that have been described and illustrated.

The invention claimed is:

1. A method of delivering a nutritional or therapeutic amount of vitamin D to a human being, said method comprising:
   (i) applying one drop of a composition consisting of a nutritional or therapeutic effective amount of 9 to 9000 mcg/ml vitamin D in a liquid triglyceride of 6 to 12 carbon chain length, to an exterior surface of an object, wherein said drop adheres to the surface of said object; and
   (ii) having said human being suck or lick said composition directly from said object.

2. A method as claimed in claim 1, wherein said human being is an adult and said object is the skin of an arm or hand of said adult.

3. A method as claimed in claim 1, wherein said human being is an infant and said object is a woman's nipple or the external surface of a pacifier.

4. A method according to claim 1, wherein the composition consists of from 150 to 450 mcg/ml vitamin D in a liquid triglyceride of 6 to 12 carbon chain length.

5. A method according to claim 1, wherein said triglyceride comprises at least 95% triglycerides having a carbon-chain length selected from 8 to 10.

6. A method of delivering a nutritional or therapeutic amount of vitamin D to a human being, said method comprising:
   (i) applying one drop of a composition consisting of a nutritional or therapeutic effective amount of 9 to 9000 mcg/ml vitamin D, and a compound selected from the group consisting of a free fatty acid, a monoglyceride and an anti-oxidant preservative, in a liquid triglyceride of 6 to 12 carbon chain lengths, to an exterior surface of an object, wherein said drop adheres to the surface of said object; and
   (ii) having said human being suck or lick said composition directly from said object.

7. A method according to claim 6, wherein said compound is selected from the group consisting of caprylic acid, caprylic monoglyceride and monocaprylin.

8. A method according to claim 6, wherein said compound is at a concentration selected from 0.1% to 20% w/w of total weight of the composition.

9. A method according to claim 6, wherein said compound is at a concentration selected from 1% to 10% w/w of total weight of the composition.

10. A method of delivering a nutritional or therapeutic amount of vitamin D to a human being, said method comprising:
    (i) applying one drop of a composition consisting of a nutritional or therapeutic effective amount of 9 to 9000 mcg/ml vitamin D, and a nutritionally effective amount of a fat-soluble vitamin, in a liquid triglyceride of 6 to 12 carbon chain lengths, to an exterior surface of an object, wherein said drop adheres to the surface of said object; and
    (ii) having said human being suck or lick said composition directly from said object.

11. A method as claimed in claim 10 wherein said fat-soluble vitamin is selected from the group consisting of alpha-tocophenol (vitamin E), vitamin A, vitamin K and β-carotene.

12. A method according to claim 1, wherein the composition consists of 300 mcg/ml vitamin D in a liquid triglyceride of 6 to 12 carbon chain length.

* * * * *